United States Patent
Magerl et al.

(10) Patent No.: US 7,419,714 B1
(45) Date of Patent: Sep. 2, 2008

(54) COMPOSITE OF POLYMER OR CERAMIC MATERIALS AND COMPONENT MADE OF SUCH A COMPOSITE

(75) Inventors: Fritz Magerl, St. Gallen (CH); Roger Roland Tognini, Widnau (CH); Erich Wintermantel, Fislisbach (CH); Jörg Mayer, Niederlenz (CH); Thomas Andreas Peter, Nänikon (CH); Walter Spirig, Platz-Walzenhausen (CH)

(73) Assignee: Sepitec Foundation, Vaduz (LI)

( * ) Notice: Subject to any disclaimer, the term of this patent is extended or adjusted under 35 U.S.C. 154(b) by 0 days.

(21) Appl. No.: 09/701,104

(22) PCT Filed: May 26, 1999

(86) PCT No.: PCT/EP99/03618

§ 371 (c)(1), (2), (4) Date: Apr. 24, 2001

(87) PCT Pub. No.: WO99/61081

PCT Pub. Date: Dec. 2, 1999

(30) Foreign Application Priority Data

May 27, 1998 (DE) .................................. 198 23 737

(51) Int. Cl.
*B29C 70/40* (2006.01)
(52) U.S. Cl. ................. 428/131; 428/292.1; 428/293.4; 428/297.4; 428/299.1; 623/11.11; 623/16.11; 623/22.11; 623/23.56; 623/23.58
(58) Field of Classification Search ................. 428/131, 428/292.1, 293.4, 297.4, 299.1; 623/11.11, 623/16.11, 22.11, 23.53, 23.56, 23.58, 23.59
See application file for complete search history.

(56) References Cited

U.S. PATENT DOCUMENTS

| | | | | |
|---|---|---|---|---|
| 4,255,478 A | * | 3/1981 | Crane | 428/113 |
| 4,629,746 A | | 12/1986 | Michl et al. | 523/117 |
| 4,662,887 A | | 5/1987 | Turner et al. | 623/16 |
| 4,714,721 A | | 12/1987 | Franek et al. | 523/113 |
| 4,963,151 A | * | 10/1990 | Ducheyne et al. | 623/23.62 |
| 5,443,513 A | | 8/1995 | Moumene et al. | 623/16 |
| 5,714,105 A | | 2/1998 | Gysin et al. | 264/257 |
| 5,919,044 A | * | 7/1999 | Sicurelli et al. | 433/220 |

FOREIGN PATENT DOCUMENTS

| | | |
|---|---|---|
| DE | 3602721 | 8/1987 |
| DE | 3904595 | 4/1990 |
| DE | 4230339 | 3/1994 |
| EP | 0551574 | 7/1993 |
| EP | 0272901 | 7/1996 |
| FR | 2555902 | 6/1985 |
| GB | 2203342 | 10/1988 |
| WO | 9619336 | 6/1996 |

\* cited by examiner

*Primary Examiner*—Alicia Chevalier
(74) *Attorney, Agent, or Firm*—Volpe and Koenig P.C.

(57) ABSTRACT

A composite of polymer or ceramic material has reinforcing fibers. The composite is for use in manufacturing medical implants like osteosynthesis plates, endoprostheses, screw coupling elements, surgical instruments, and similar components. The fibers and fibrous parts are made from a material that absorbs X-rays so that it can be seen during X-ray examination.

16 Claims, 1 Drawing Sheet

COMPOSITE OF POLYMER OR CERAMIC MATERIALS AND COMPONENT MADE OF SUCH A COMPOSITE

The invention relates to a composite of polymer or ceramic material with a content of integrated reinforcing elements in the form of fibers or fibrous parts, for the manufacture of components exposed to tensile, bending, shear, compressive and/or torsional stress for use in implants, e.g., osteosynthesis plates, endoprostheses, screw coupling elements, in surgical instruments, etc. and component made of such a composite.

Composites having the most varied of composition are achieving a steadily growing acceptance as implants precisely in the area of surgery. Advantageous knowledge can be gained during manufacture already, particularly since shrinking during polymerization is being improved relative to pure plastics. Mechanical strength values, e.g., compressive strength, rigidity and modulus of elasticity. In addition, the thermal expansion coefficient can be reduced in comparison to pure plastic.

For example, EP-A-0 551 574 shows a multiple-layer composite for achieving high strength made out of thermoplastics, e.g., polyaryl ketones, which contains braided metal fibers, so that the implant can be easily detected with X-rays.

EP-A-0 572 751 describes an endoprosthesis comprised of a compact, thermoplastic composite made out of thermoplastics, e.g., polyarylether ketone and continuous fibers (with areas of varying fiber orientation), wherein the endoprosthesis contains a metal lattice.

GB-A-2 203 342 describes an implant, e.g., made out of woven polyester, which contains a metal (Au, Pt, Ti, Pd) as a wire or lattice to enable detection.

One often perceived disadvantage to such components fabricated out of composites is that the used implants, e.g., osteosynthesis plates, bone screws, etc., cannot be detected during X-ray examination. It is precisely for this reason that implants consisting of metal or metal parts are often still used.

The use of an X-ray opaque material is already known in dental technology, which is intended to make a corresponding dental filling material visible during X-rays, such a material cannot be used for implants that must exhibit a corresponding strength and have a correspondingly high percentage of strength-increasing fibers. If an X-ray opaque filler were then to be additionally introduced into the matrix material, there would no longer be any guarantee that the used fibers are still correctly embedded. This would substantially diminish the strength of such a component. It is simply not possible to incorporate other fillers into a fiber-reinforced composite in addition to the fibers.

SUMMARY

Therefore, the object of this invention is to provide a composite of the kind mentioned at the outset that enables the attainment of identical or even in part improved strength characteristics for the components made out of the composite, while additionally permitting a good visibility during X-ray diagnostics.

According to the invention, the object is achieved by having the polymer or ceramic material incorporate at least a small percentage of the content of reinforcing elements, e.g., in the form of fibers or fibrous parts made out of a material with a higher X-ray absorption.

Despite the existence of additional reinforcing elements with a higher X-ray absorption, or also the complete or partial replacement with already present reinforcing elements, this measure yields a strength for the composite equal to or even better than the previous configuration. The reinforcing elements with a higher X-ray absorption are also fibers or fibrous parts, which, in addition to now enabling X-ray diagnostics, yield a corresponding strength in the implants. These fibers or fibrous parts consisting of a material with a higher X-ray absorption enable X-ray visibility, as a rule without disrupting other imaging procedures, like CT, NMR, MRI, etc. The fibers or fibrous parts are also non-disruptive during radiation treatment, since they produce no relevant shadowing effect. However, the significant advantage lies precisely in the fact that the fibers or fibrous parts with a higher X-ray absorption yield an increased strength in the implants made out of them. By contrast, other fillers or X-ray opaque mixtures, e.g., particulate metal oxides, diminish the strength.

It is additionally proposed for the composite that it consist of a polymer or ceramic material with a high fiber percentage, primarily using continuous, long or short fibers, wherein at least a small percentage of fibers or fibrous parts consist of a material with a high X-ray absorption. Despite a very high percentage of continuous fibers, the volume percentage of residual material can be retained, and the existing strength characteristics can be retained or even enhanced through the sole replacement of otherwise present fibers with fibers consisting of a material with a high X-ray absorption.

In one advantageous design, the composite is prefabricated as a rod material consisting of thermoplastic materials with carbon fibers and fibers made out of a material with a high X-ray absorption, and can be or has been molded into a shape required for the final component in a thermoforming process. Despite the special composition with fibers comprised of varying materials, good thermoformability can be retained, thereby enabling an optimal production of even relatively complicated components even with a composite improved in this manner.

In one embodiment, it is proposed that the composite consist of carbon fiber-reinforced PAEK (poly-aryl-ether-ketone) and a percentage of fibers made out of a material with a high X-ray absorption. This makes it a material with a special compatibility, high strength and the visibility necessary for X-ray diagnostics.

Optimal strength levels can be achieved by designing the carbon fibers and fibers made out of a material with a higher X-ray absorption as continuous fibers and/or fibers with a length exceeding 3 mm.

To enable a transfer of force between the fibers and the other material of the composite, i.e., to also ensure an optimal strength at a high volume density of fibers, it is provided that the used fibers be enveloped on the surface by the matrix material both in the preform and the finished component.

Steel fibers could in themselves also be used as an X-ray opaque material, but would then end up giving rise to other problems for implants, e.g., artifacts in an MRI, NMR, etc. Therefore, the fibers or fibrous parts comprised of a material with a high X-ray absorption are advantageously made out of a nonmagnetic material.

Therefore, it is viewed as particularly advantageous for the fibers or fibrous parts with high X-ray absorption to consist of tantalum, tungsten, gold, platinum, etc., meaning of a metal or metal oxides with a high attenuation coefficient.

The component according to the invention made out of such a composite is characterized by the fact that, a predictable progression and predictable quantity and orientation of reinforcing elements in the form of fibers or fibrous parts made out of a material with a high X-ray absorption, are provided, tailored to the shape and application of the component. Therefore, it is possible to graduate the visibility of the component, i.e., of an implant. Depending on the segments of an implant where a stronger, weaker or even no X-ray visibility is desired, it is possible to control the application and used quantity of fibers made out of X-ray opaque materials. Hence, the ability to concentrate or accumulate these fibers is of particular importance.

In this connection, it is then also possible that areas of differing fiber orientation or fiber progression are provided relative to the longitudinally or transverse oriented alignment of the component. This can also be a positive influence on an even more informative X-ray diagnostics.

In one special design variant, the ratio of carbon fibers to fibers or fibrous parts made out of a material with a high X-ray absorption can be or is variable at a total fiber percentage of 50% v/v, for example, depending on the application requirement. Therefore, a component with the same or even better strength values is achieved, even though the overall volume percentage of the fibers is not increased.

So that components can be precisely adjusted to the conditions for use, it is proposed that the total fiber percentage in the composite remains constant over their length or width, but this changes the ratio of carbon fibers to fibers or fibrous parts made out of a material with a high X-ray absorption, depending on the application requirement. Therefore, the visibility can be deliberately controlled for an optimal X-ray diagnostics, without impairing the strength values.

However, it is also possible within the framework of the invention to vary the stiffness of the connecting element by varying the orientation of used fibers from the force application point toward the free end. This can be desired in a connecting element, e.g., a screw, if various areas are to exhibit a greater flexibility than other sections during use. This also enables a precise adjustment to the conditions existing in the area of a bone.

In this case, it is not only possible to smoothly adjust the strength of such a component. It is also proposed that the stiffness of the component be incrementally or continuously tapered by varying the orientation of the fibers viewed from the force application point to the free end.

In a special design variant of a component in the form of a strip or plate assembly part, e.g., an osteosynthesis plate, it is proposed that a concentration of fibers be present in the area of one or more recesses or holes in the component, wherein the percentage of fibers or fibrous parts made out of a material with a high X-ray absorption is reduced in these areas, if necessary. Therefore, it can be ensured that there will also not be a strong concentration of fibers made out of a material with a high X-ray absorption in an area with a highly concentrated arrangement of fibers. Under certain conditions, this would not be conducive for a targeted X-ray diagnostics. By contrast, this can be achieved by keeping the content of fibers made out of a material with a high X-ray absorption constant as desired over the entire length and/or width of a component, meaning also in the area of recesses or holes.

Therefore, the application of the composite according to the invention and its use in manufacturing components according to the invention has created numerous new ways of performing an optimal X-ray diagnostics when using implants made out of such materials.

BRIEF DESCRIPTION OF THE DRAWINGS

Additional details will be explained in even greater detail in the description below. Shown on.

DETAILED DESCRIPTION OF THE PREFERRED EMBODIMENTS

Figure 1:
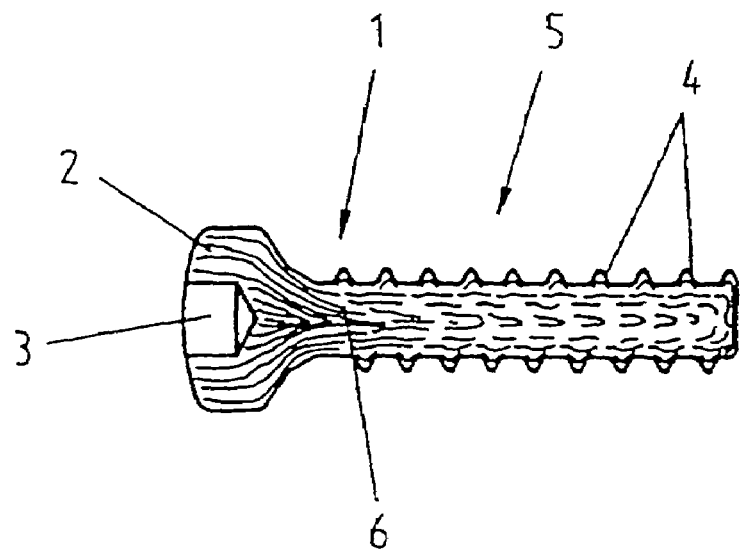
FIG. 1 is a component in the form of a bone screw.

On the one hand, this invention involves a composite consisting of polymer or ceramic material with a content of integrated reinforcing elements in the form of fibers or fibrous parts, for the manufacture of components exposed to tensile, bending, shear, compressive and/or torsional stress for use in implants, e.g., osteosynthesis plates, endoprostheses, screw coupling elements, in surgical instruments, as already enumerated above. In this case, it is regarded as essential to provide at least a small percentage of the content of fibers or fibrous parts made out of a material whose X-ray absorption is higher than the that of the remaining fibers or fibrous parts in the polymer or ceramic material.

In one embodiment, the composite consists of a polymer or ceramic material with a fiber percentage of more than 50% v/v, with primarily continuous fibers being used. At least a small share of fibers or fibrous parts consists of a material with a higher X-ray absorption than that of the remaining fibers or fibrous parts. In this case, prefabrication can take place as a profiled rod material comprised of thermoplastics with carbon fibers and fibers made out of a material with a high X-ray absorption. Final production of the component out of the composite then takes place in a thermoforming process. Therefore, the material is pressed into a shape required for the final component. In one special variant, the composite consists of carbon fiber-reinforced PAEK (poly-acryl-ether-ketones) and a percentage of fibers made out of a material with a higher X-ray absorption. Even though the fibers consist of a material with a higher X-ray absorption, optimal processability is retained, and no additional tool wear comes about. Not only does this enable processing via pressing in a thermoforming procedure, fabrication in an injection molding process is also possible.

Use of the composite also ensures the biocompatibility of the finished component.

The fibers or fibrous parts made out of a material with a higher X-ray absorption in the composite are formed out of a nonmagnetic material. Particularly suited here are fibers or fibrous parts with a high X-ray absorption comprised of tantalum, tungsten, gold, platinum, etc., meaning a metal with a high attenuation coefficient. Within the framework of the invention, it would also be conceivable to use ceramic fibers made of oxides of elements with a high X-ray absorption, for example. Fibrous parts can also include long or short fibers, or additional other fillers to be used without lowering the strength. With respect to the existing reinforcing elements, it is possible to use the same or similar reinforcing elements in the form of fibers or fibrous parts. "Similar" here denotes the same or similar dimension and/nor same or similar mechanical properties.

The essence of the invention can only be illustrated on a small scale in the depictions shown on the drawing. The following explanations therefore become necessary. The component 1 in the form of a screw shown on FIG. 1 essentially consists of a head 2, force application point 3 for introducing the force from a lathe tool, and a shank 5 furnished with a thread 4. The key factor in such a component 1 is the special progression and arrangement of continuous fibers 6. Selecting a composite of thermoplastics with carbon fibers makes it possible to fabricate a light, X-ray transparent and biocompatible connecting element. However, in order to make this connecting element precisely during X-ray diagnostics, the measures described in the invention are necessary, namely having a portion of the fibers 6 consist of a material with a high X-ray absorption.

Figure 2:
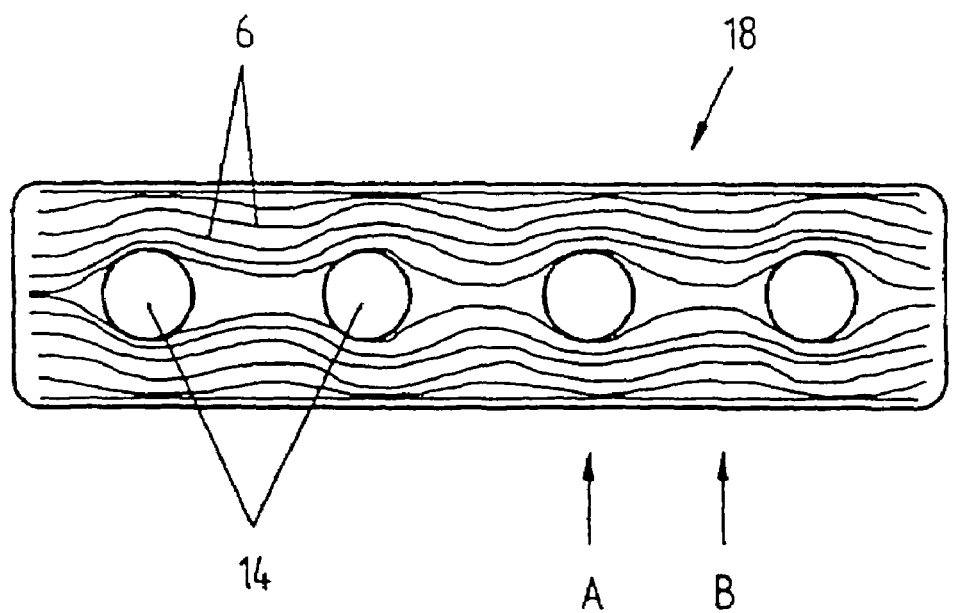
FIG. 2 is a component in the form of an osteosynthesis plate.

The measures according to the invention can be implemented for practically all implants, meaning also for rail or plate-shaped components 18. FIG. 2 diagrammatically depicts such a component 18 in the form of an osteosynthesis plate. Through holes 14, indentations, blind holes, etc. are provided in such components, which then are surrounded in a special manner by the fibers. Without taking any additional measures aimed at deliberately controlling the quantity and alignment of fibers 6, a denser arrangement of fibers 6 arises in the normally weakened zones A, so that these zones A have the same strength or stiffness as the other areas B of such a component. During fabrication in a thermoforming process, in particular via push-pull extrusion, the progression and alignment of the fibers 6 can still be additionally controlled, and hence influenced.

All used fibers 6, or at least a large percentage of them, i.e., the carbon fibers and fibers made out of a material with a higher X-ray absorption, are advantageously designed as continuous fibers or fibers with a length exceeding 3 mm. In this case, care is taken for strength reasons to envelop the surface of the incorporated fibers by the matrix material in both the perform and finished component.

In the component 1 or 18 to be manufactured out of a composite, e.g., a screw according to FIG. 1 or an osteosynthesis plate according to FIG. 2, a predictable progression and predictable quantity and orientation of reinforcing elements in the form of fibers 6 or fibrous parts made out of a material with a higher X-ray absorption, are provided, tailored to the shape and application of the component 1 or 18. In addition, areas of varying fiber orientation or varying fiber progression can also be provided relative to the longitudinally or transverse oriented alignment of the component 1 or 18.

Finally, at a total fiber percentage of 50% v/v in a component 1 or 18, for example, the ratio of carbon atoms 6 to fibers 6 or fibrous parts made out of a material with a high X-ray absorption can be or has been altered, depending on the application requirement. It is also possible to distribute the total fiber percentage in the composite uniformly over the length and width of a component 1 or 18, but the ratio of carbon fibers 6 to fibers 6 or fibrous parts made out of a material with a high X-ray absorption changes as needed and depending on the application requirement. It is also possible to vary the stiffness of the connecting element by varying the orientation of used fibers from the force application point toward the free end. In another possible variant, the stiffness of the component is incrementally or continuously tapered by varying the orientation of the fibers viewed from the force application point to the free end.

Precisely in a component 18 designed as a strip or plate-shaped assembly piece, e.g., an osteosynthesis plate of the kind shown on FIG. 2, a concentration of fibers 6 is present in the area A of one or more recesses 14 or holes. If needed, it is here possible to reduce the percentage of fibers 6 or fibrous parts made out of a material with a higher X-ray absorption in these areas A. By contrast, if the percentage of fibers made out of a material with a higher X-ray absorption is also not reduced in the area of this concentration of fibers, even better contrasts can be achieved while targeting during the use of X-rays.

The invention claimed is:

1. A surgically implantable biocompatible component comprising:
   a composite of polymer or ceramic material;
   X-ray absorbing reinforcing fibers distributed throughout the composite, wherein an orientation of the X-ray absorbing reinforcing fibers is tailored to a shape and application of the surgically implantable biocompatible component (1, 18) in a defined manner to provide X-ray visibility control for the surgically implantable biocompatible component; and
   carbon fibers, wherein a total fiber percentage in the composite remains constant over a length or width of the biocompatible component, which changes a ratio of carbon fibers (6) to X-ray absorbing fibers (6).

2. Component according to claim 1, wherein the composite is prefabricated as a profiled rod material further comprising carbon fibers.

3. Component according to claim 2, wherein the carbon fibers and the X-ray absorbing fibers are designed as continuous fibers and/or fibers with a length exceeding 3 mm.

4. Component according to claim 1, wherein the polymer material is PAEK (poly-aryl-ether ketone).

5. Component according to claim 1, wherein the fibers are enveloped by a matrix of the polymer or ceramic material.

6. Component according to claim 1, wherein the X-ray absorbing fibers comprise a nonmagnetic material.

7. Component according to claim 1, wherein the X-ray absorbing fibers are made from materials selected from the group consisting of: tantalum, tungsten, gold, and platinum.

8. Component according to claim 1, wherein the fibers are oriented differently depending on the longitudinally or transverse oriented alignment of the component (1, 18).

9. A surgically implantable biocompatible component in the form of a strip or plate assembly part comprising:
   a composite of polymer or ceramic material;
   X-ray absorbing reinforcing fibers distributed throughout the composite, wherein an orientation of the X-ray absorbing reinforcing fibers is tailored to a shape and application of the surgically implantable biocompatible component (1, 18) in a defined manner to provide X-ray visibility control for the component;
   wherein a concentration of fibers (6) is present in an area (A) of one or more recesses (14) or holes in the biocompatible component (18), and wherein the percentage of the X-ray absorbing fibers is reduced in the area (A).

10. Component according to claim 9, wherein the composite is prefabricated as a profiled rod material further comprising carbon fibers.

11. Component according to claim 10, wherein the carbon fibers and the X-ray absorbing fibers are designed as continuous fibers and/or fibers with a length exceeding 3 mm.

12. Component according to claim 9, wherein the polymer material is PAEK (poly-aryl-ether ketone).

13. Component according to claim 9, wherein the fibers are enveloped by a matrix of the polymer or ceramic material.

14. Component according to claim 9, wherein the X-ray absorbing fibers comprise a nonmagnetic material.

15. Component according to claim 9, wherein the X-ray absorbing fibers are made from materials selected from the group consisting of: tantalum, tungsten, gold, and platinum.

16. Component according to claim 9, wherein the fibers are oriented differently depending on the longitudinally or transverse oriented alignment of the component (1, 18).

\* \* \* \* \*